United States Patent [19]

Zadina

[11] 4,084,267
[45] Apr. 18, 1978

[54] DRIVE FOR AN ORTHOSIS OR A PROSTHESIS

[75] Inventor: Alfred Zadina, Vienna, Austria

[73] Assignee: Viennatone Gesellschaft m.b.H., Vienna, Austria

[21] Appl. No.: 724,870

[22] Filed: Sep. 20, 1976

[30] Foreign Application Priority Data

Sep. 18, 1975 Austria ............................ 7183/75

[51] Int. Cl.² ............................ A61F 1/06; A61F 1/00; A61F 5/10
[52] U.S. Cl. ............................ 3/1.1; 3/12.5; 3/12.6; 128/77
[58] Field of Search ............................ 3/1.1, 12–12.7; 128/77

[56] References Cited

U.S. PATENT DOCUMENTS

| | | | |
|---|---|---|---|
| 2,516,791 | 7/1950 | Motis et al. | 3/12.5 |
| 3,466,937 | 9/1969 | Motis | 3/12.5 X |
| 3,864,983 | 2/1975 | Jacobsen | 3/1.1 X |
| 3,866,246 | 2/1975 | Seamone et al. | 3/1.1 |
| 3,967,321 | 7/1976 | Ryan et al. | 3/1.1 |

FOREIGN PATENT DOCUMENTS 674,024   4/1966   Belgium ............................ 3/1.1

*Primary Examiner*—Ronald L. Frinks
*Attorney, Agent, or Firm*—Kurt Kelman

[57] ABSTRACT

A movable limb rehabilitation device such as an orthosis or prosthesis part is connected to a drive by a transmission which converts rotary into linear reciprocatory motion. The transmission includes a cylinder coupled to the drive for rotation therewith and having two separate threads of opposite pitch, a sleeve and a spindle respectively threadedly mounted on the threads for linear movement in relation to the cylinder and non-rotatably held on the cylinder whereby rotation of the cylinder by the drive causes the linear movement of the sleeve and spindle, and a tackle with a cable or chain having two ends facing the drive, the ends being respectively affixed to the sleeve and spindle and the tackle being connected to the movable orthosis or prosthesis part for moving the same in response to the rotary motion of the drive.

14 Claims, 7 Drawing Figures

U.S. Patent April 18, 1978 Sheet 1 of 2 4,084,267
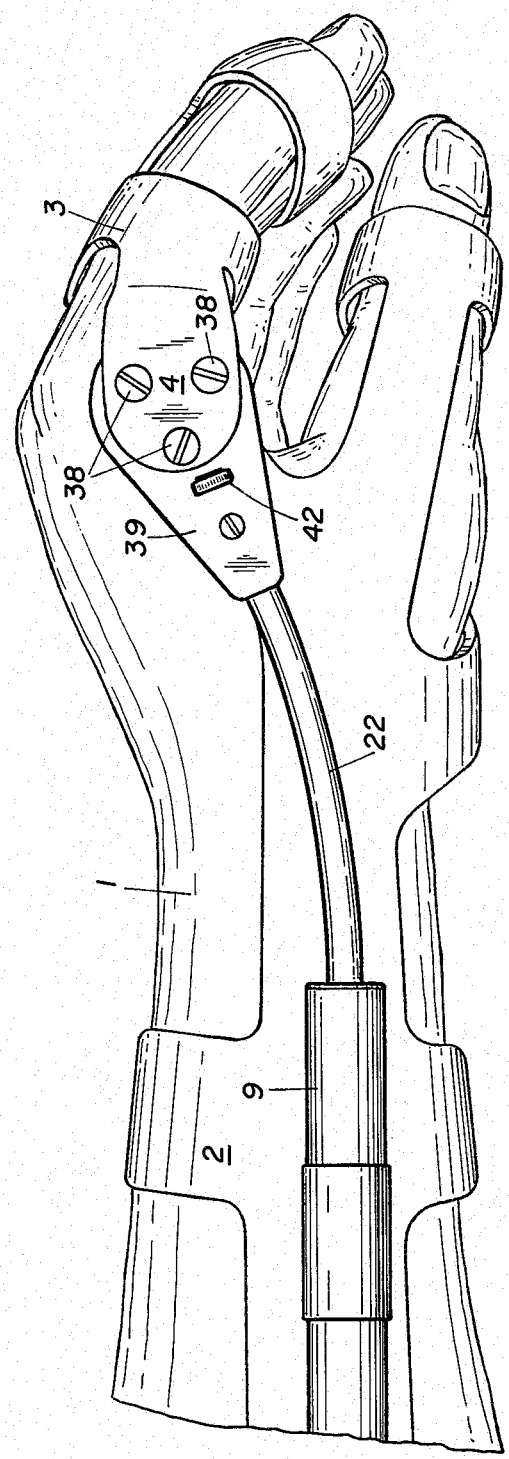
FIG.1
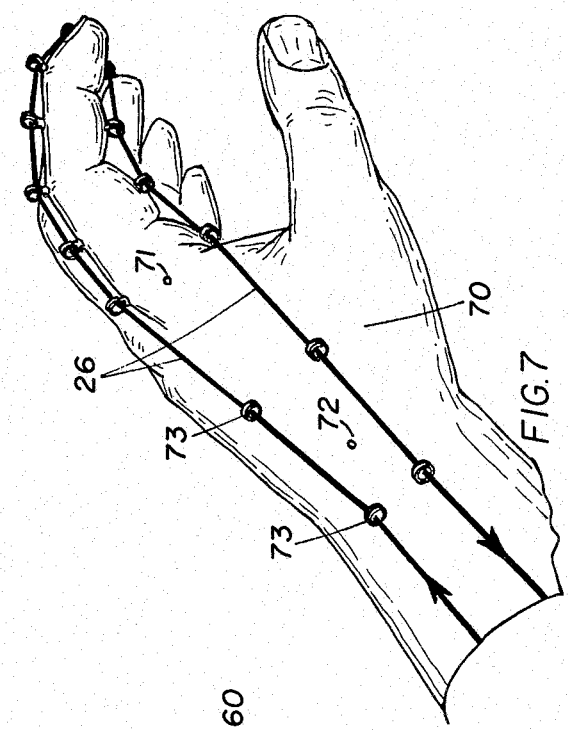
FIG.7
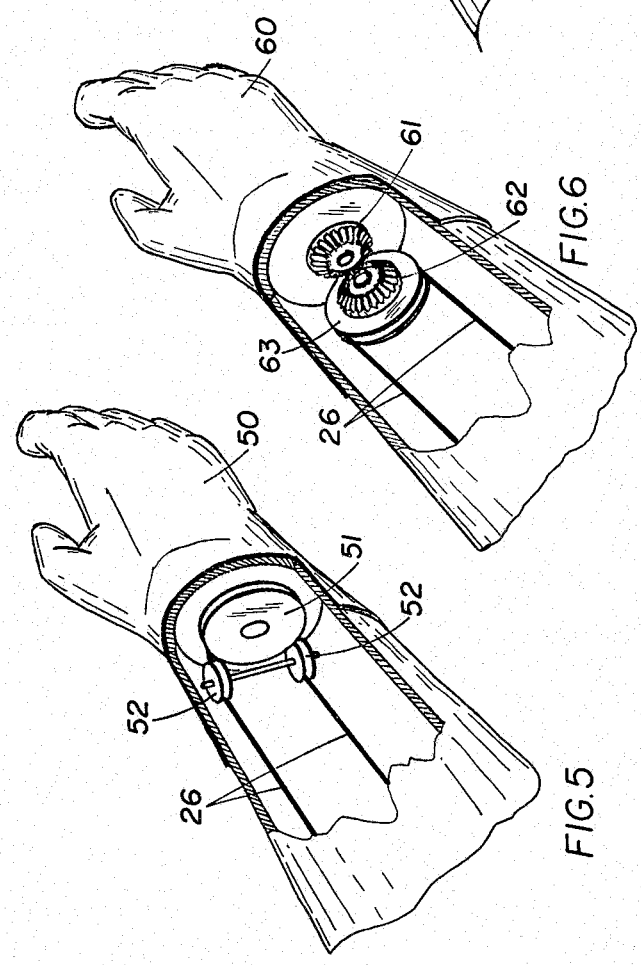
FIG.6
FIG.5

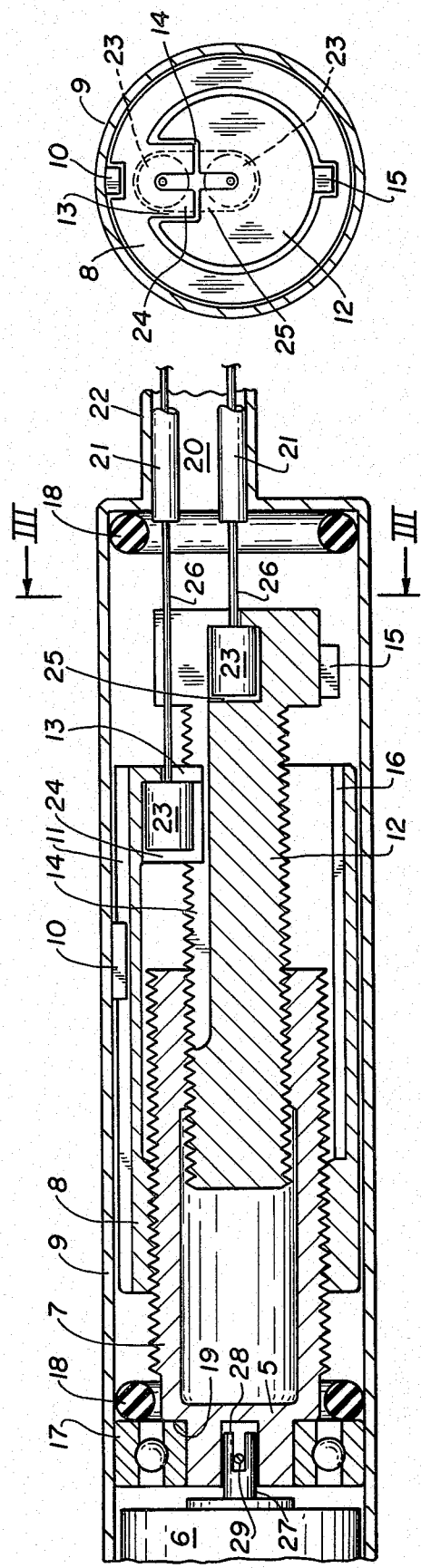
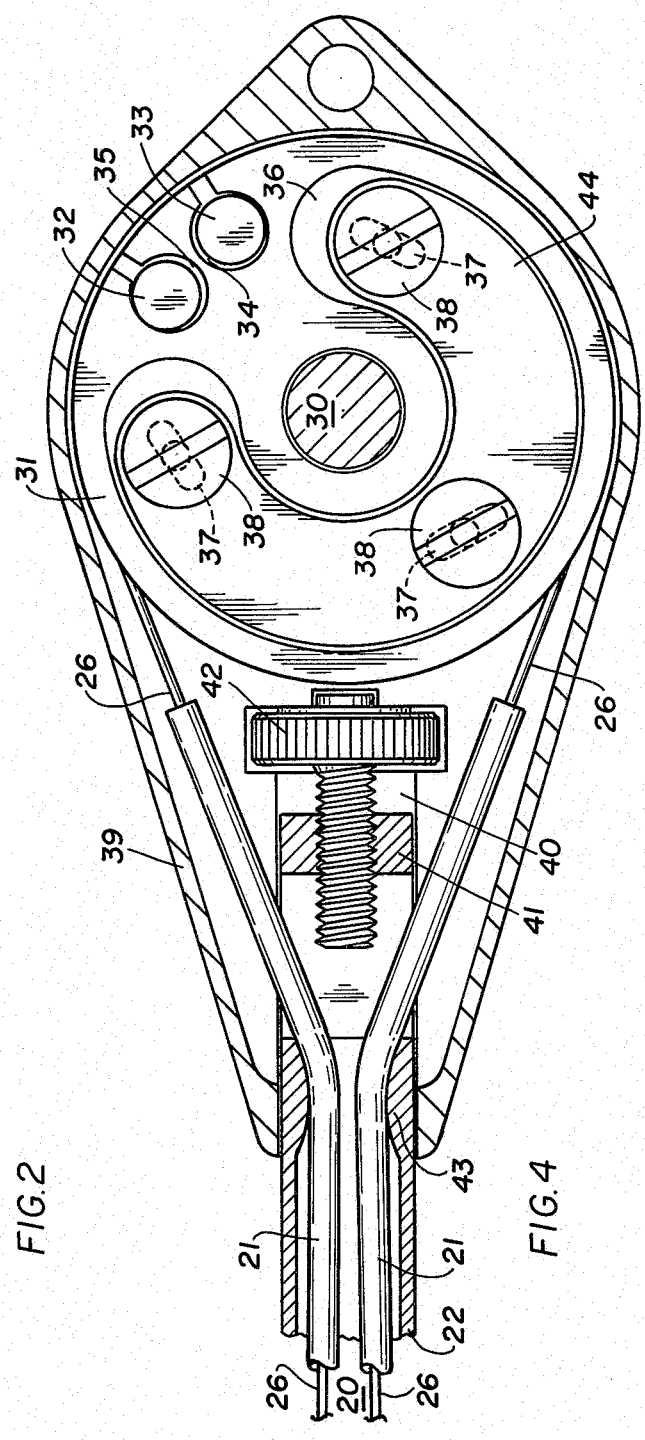

DRIVE FOR AN ORTHOSIS OR A PROSTHESIS

The present invention relates to an improved transmission in a limb rehabilitation device such as an orthosis or prosthesis which comprises a stationary part and a part movably mounted on the stationary part and a drive unit mounted on the stationary part, the transmission being designed to convert a rotary motion of the drive unit into a reciprocating linear motion for driving the movably mounted part. A tackle connects the transmission and the movably mounted prosthesis part for moving the same in response to the rotary motion of the drive unit.

Known transmission of this type provide for the reciprocatory motion to be effected in one linear direction against the bias of a spring. This causes a loss of power because the spring bias must be overcome during this movement and such a drive is, therefore, inefficient. In addition, to maintain uniform tensile forces over the entire stroke of reciprocation, springs of considerable length must be used, which requires much space and further reduces the efficiency of the prosthesis.

It is the primary object of this invention to overcome these disadvantages and provide a limb rehabilitation device such as an orthosis, or prosthesis of the indicated type which is efficient in operation.

This and other objects are accomplished according to the invention with a transmission which includes a transmission member having two separate threads of opposite pitch, and two transmission elements respectively threadedly mounted on a respective thread of opposite pitch for linear movement in relation thereto, the transmission elements being non-rotatable in relation to the transmission member whereby rotation of the member causes the linear movement of the elements. The tackle with flexible elongated motion-transmitting means has two ends facing the drive unit and a respective one of the motion-transmitting means ends is affixed to a respective one of the transmission elements.

The above and other objects and features of the present invention will be more fully explained in the following detailed description of certain now preferred embodiments thereof, taken in conjunction with the accompanying drawing wherein FIG. 1 is a perspective view of an orthosis according to one embodiment of this invention, mounted on an arm of a patient;

FIG. 2 is an axial section showing a specific embodiment of the transmission;

FIG. 3 is a transverse section along line III—III of FIG. 2;

FIG. 4 shows a sectional view of the drive connection for the movably mounted part of the orthosis; and FIGS. 5 to 7 are simplified perspective views of three embodiments of flexible elongated motion-transmitting means and their respective attachments to the drive connection for a movably mounted prosthesis part.

FIG. 1 illustrates stationary orthosis part 2 which is mounted on arm 1 of a patient and includes a portion supporting the thumb of the patient's hand. Orthosis part 3 supports a finger of the patient's hand and is movably mounted on stationary part 2 by pivotal joint 4 to be described hereinafter in connection with FIG. 4, this pivot being arranged in the region of the natural joint connecting the finger to the hand. The drive unit and transmission are enclosed in housing 9 mounted on the stationary orthosis part and the transmission is coupled to the joint 4 by an elongated flexible motion-transmitting means enclosed in tubular housing 22, as will be more fully described hereinafter in connection with FIGS. 2 to 4.

As shown in FIG. 2, drive unit 6 comprising any suitable motor for producing a rotary motion and drive shaft 27 is arranged in housing 9. The drive shaft is coupled to transmission member 7 for rotation of the transmission member with the shaft. In the illustrated embodiment, the transmission member is a tubular cylinder open at one end, a closed end 5 of cylinder 7 having diametrically opposed notches receiving forked end 28 of drive shaft 27, pins 29 holding the forked end of the shaft in non-rotatable connection with the cylinder end for rotating the transmission cylinder 7 with the drive shaft. Cylinder end 5 defines shoulder 19 with the cylinder, and the cylinder end is rotatably mounted in ball bearing 17 sitting on the shoulder and surrounding the cylinder end.

Transmission cylinder 7 has two separate threads of opposite pitch, one of the threads being disposed on the outer cylinder wall and the other thread being disposed on the inner cylinder wall. Two transmission elements are respectively threadedly mounted on a respective one of the threads of opposite pitch for linear movement of the transmission elements in relation to the transmission cylinder, one of the transmission elements in the illustrated embodiments being exteriorly threaded spindle 12 extending through the open end into the tubular cylinder 7 and being threadedly connected to the threads on the inner cylinder wall, and the other transmission element being an interiorly threaded sleeve 8 extending over the outer cylinder wall and being threadedly connected to the threads on the outer wall.

The spindle and sleeve are non-rotatable in relation to the tubular cylinder whereby rotation of cylinder 7 causes the linear movement of spindle 12 and sleeve 8. For this purpose, block or key 10 is affixed to housing 9 and is guided in longitudinal groove 11 extending in an axial direction of the sleeve 8 on the circumference of the sleeve for holding the sleeve non-rotatable in relation to tubular cylinder 7 while lug 13 extends radially from sleeve 8 into longitudinal groove 14 extending in an axial direction of the spindle on the circumference thereof for holding the spindle non-rotatable in relation to the sleeve. A further means for holding the transmission assembly parts in non-rotatable relationship at least for a considerable portion of the linear movement includes another lug 15 extending radially from spindle 12 and a further longitudinal groove 16 extending in an axial direction in an inner wall of the sleeve. Lug 15 is guided in groove 16 during a part of the linear movement as long as the spindle is not moved sufficiently out of the cylinder that the lug is disengaged from its guide groove. During this initial stroke of the movement, the assembly is double-locked against relative rotation of its parts.

At the respective ends of the path of reciprocatory movement of sleeve 8 are mounted rubber shock absorbing rings 18 for elastically yieldingly absorbing the shock of the sleeve moving thereagainst.

Tackle 20 with flexible elongated motion-transmitting means 26 guided in flexible synthetic resin tubes 21 is arranged in tubular housing 22 which, in the illustrated embodiment, is integral with housing 9 and constitutes a constricted extension thereof. The flexible motion-transmitting means has two ends facing drive unit 6 and a respective one of the motion-transmitting means ends is affixed to a respective one of transmission elements 8 and 12. In the illustrated embodiment, anchor elements 23 are affixed to the ends of the motion-transmitting means and are received in recess 24 in sleeve 8 and recess 25 in spindle 12 for affixing the ends to these elements. The tackle is connected to the movably mounted orthosis part 3 for moving the same in response to the rotary motion of drive unit 6, this connection depending on the nature of the desired movements of movable part 3, for instance whether a bending or rotary movement is desired.

The desired movement of the finger held in orthosis part 3 in the embodiment of FIG. 1 is a bending movement and a corresponding drive connection is illustrated in FIG. 4. As shown, the flexible elongated motion-transmitting means in this embodiment comprises two elongated cables 26. Equivalent elongated flexible elements such as chains may be substituted. As is shown in FIG. 1, the ends of cables 26 facing drive unit 6 are affixed to sleeve 8 and spindle 12, respectively. The two other ends of the cables are connected to a drive connection for movably mounted orthosis part 3. This drive connection is mounted in housing 39 and comprises shaft 30 mounted on the housing and mounting pulley 31 for free rotation on the shaft. If chains were used instead of cables, the pulley would be replaced by a sprocket wheel. The two other ends of cables 26 are each trained about a portion of the circumference of idling pulley 31 and the cable ends have affixed thereto anchor elements 32 and 33, respectively, which are received in recesses 34 and 35 in the pulley for detachably connecting the other cable ends to the drive connection. The drive connection further comprises somewhat kidney-shaped element 44 of the movable finger support part 3 which is received in a similarly shaped but somewhat longer recess 36 in pulley 31. Element 44 defines slots 37 (shown in broken lines in FIG. 4) through which extend fastening screws 38 which hold movable finger support part 3 on housing 39 (see FIG. 1). In view of the mounting of the fastening screws in elongated slots and the movability of element 44 in somewhat longer recess 36, it is possible to adjust the rest position of the finger.

As shown in FIG. 4, housing 22 has a lining with an annular bead 43 at one end thereof for facilitating guidance of the cables in their guide tubes 21. Housing 22 extends into an axial recess 40 in housing 39.

FIG. 4 also shows a tensioning device for cables 26 arranged to cause relative movement between housing 22 and housing 39 in the direction of elongation of the cables for tensioning the same, if desired. The illustrated tensioning device comprises nut 41 affixed to the end of housing 22 and threadedly engaged by set screw 42 whose knurled head (as shown in FIG. 1) extends outside housing 39. Rotation of the set screw will cause the required relative movement of housing 22 to housing 39 for tensioning the cables. As will be obvious, the tensioning device structure is independent of any specific drive connection for movable orthosis part 3 and may, therefore, also be used in the embodiments thereof described hereinafter in connection with FIGS. 5 and 6.

The drive connection shown in FIGS. 5 and 6 is designed for rotary motion of a movable prosthesis part, rather than the bending motion provided by the embodiment of FIG. 4. Thus, the prosthesis joint provided to replace the natural hand joint is a rotary joint.

In the embodiment of FIG. 5, pulley 51 is affixed to prosthetic hand 50, the two ends of cables 26 being trained over and attached to the pulley in the manner fully described in connection with FIG. 4. The cables are guided to the pulley by guide rollers 52 and the idling pulley is mounted for free rotation on hand 50 which is detachably mounted on the housing for the tackle.

A functionally equivalent embodiment is illustrated in FIG. 6 wherein the idling pulley is replaced by a bevel gearing comprising driving bevel gear 62 meshing with driven bevel gear 61. The ends of cables 26 are again attached in the manner of FIG. 4 to a pulley 63 which carries driving bevel gear 63. Hand 60 carries driven bevel gear 61 and is mounted for free rotation on the housing for the tackle.

In the embodiment of FIG. 7, the drive connection is constituted by cables 26 themselves whose other ends form an end portion opposite to the ends facing drive unit 6. These ends are attached to different sides of a finger of prosthetic hand 70 which has bending joints 71 and 72 at the points usual in normal hands and fingers. The cable ends are attached to the finger in the region of its tip and the cables are guided in eyes 73 which may be provided in longitudinal grooves extending along hand 70. The eyes could also be carried by a support glove to which the cable ends would be attached. In this manner, the fingers, except for the thumb, may be bent directly.

What is claimed is:

1. A limb rehabilitation device comprising a stationary part and a part movably mounted on the stationary part, a drive unit mounted on the stationary part and a transmission for converting a rotary motion produced by the drive unit into a reciprocating linear motion for driving the movably mounted part, the transmission including a transmission member coupled to the drive unit for rotation therewith, the transmission member having two separate threads of opposite pitch, two transmission elements respectively threadedly mounted on a respective one of the threads of opposite pitch for linear movement in relation thereto, the transmission elements being non-rotatable in relation to the transmission member whereby rotation of the member causes the linear movement of the elements, and a tackle with flexible elongated motion-transmitting means having two ends facing the drive unit, a respective one of the motion-transmitting means ends being affixed to a respective one of the transmission elements and the tackle being connected to the movably mounted part for moving the same in response to the rotary motion of the drive unit.

2. The limb rehabilitation device of claim 1, wherein the transmission member is a tubular cylinder having an outer and an inner wall, and being open at an end facing the tackle, one of the threads being disposed on the outer cylinder wall and the other thread being disposed on the inner cylinder wall, one of the transmission elements is a threaded spindle extending through the open end into the tubular cylinder and being threadedly connected to the threads on the inner cylinder wall, and the other transmission element is an interiorly threaded sleeve extending over the outer cylinder wall and being threadedly connected to the threads on the outer wall.

3. The limb rehabilitation device of claim 2, wherein one of the ends of the threaded spindle and sleeve each defines a recess, and further comprising anchor elements affixed to the ends of the motion-transmitting means, the anchor elements being received in the recesses.

4. The limb rehabilitation device of claim 2, further comprising a stationary key guided in a longitudinal groove extending in an axial direction of the sleeve for holding the sleeve non-rotatable in relation to the tubular cylinder, and a lug extending radially from the sleeve into a longitudinal groove extending in an axial direction of the spindle for holding the spindle non-rotatable in relation to the sleeve.

5. The limb rehabilitation device of claim 4, further comprising another lug extending radially from the spindle and the sleeve defining a further longitudinal groove extending in an axial direction in an inner wall thereof, the other lug being guided in the further longitudinal groove during at least a part of the linear motion for additionally holding the sleeve and spindle non-rotatable in relation to the tubular cylinder.

6. The limb rehabilitation device of claim 4, further comprising a housing wherein the tubular cylinder, sleeve and spindle are arranged coaxially, the key being mounted on the housing.

7. The limb rehabilitation device of claim 6, further comprising elastically yielding shock absorbing means in the housing for limiting the linear reciprocating motion of the sleeve.

8. The limb rehabilitation device of claim 1, wherein the flexible elongated motion-transmitting means comprises two elongated flexible elements each having two ends, the ends of the flexible elements facing the drive unit being affixed to respective ones of the transmission elements, and further comprising a drive connection for the movably mounted part, the other ends of the flexible elements being connected to the drive connection.

9. The limb rehabilitation device of claim 8, wherein the other ends of the flexible elements are detachably connected to the drive connection.

10. The limb rehabilitation device of claim 8, further comprising a housing for the tubular transmission member and elements, a second housing for the flexible elongated motion-transmitting means, and a third housing for the drive connection, and a tensioning device for the motion-transmitting means, the tensioning device being arranged to cause relative movement between the second and third housing in the direction of elongation of the motion-transmitting means for tensioning said means.

11. The limb rehabilitation device of claim 1, further comprising a drive connection for the movably mounted part and a pulley over which the flexible elongated motion-transmitting means is trained, the movably mounted part and the pulley being detachably mounted on the drive connection.

12. A prosthesis comprising a stationary part and a part movably mounted on the stationary part, a drive unit mounted on the stationary part and a transmission for converting a rotary motion produced by the drive unit into a reciprocating linear motion for driving the movably mounted part, the transmission including a transmission member coupled to the drive unit for rotation therewith, the transmission member having two separate threads of opposite pitch, two transmission elements respectively threadedly mounted on a respective one of the threads of opposite pitch for linear movement in relation thereto, the transmission elements being non-rotatable in relation to the transmission member whereby rotation of the member causes the linear movement of the elements, a tackle with flexible elongated motion-transmitting means having two ends facing the drive unit, a respective one of the motion-transmitting means ends being affixed to a respective one of the transmission elements and the tackle being connected to the movably mounted prosthesis part for moving the same in response to the rotary motion of the drive unit, a drive connection for the movably mounted prosthesis part and a pulley over which the flexible elongated motion-transmitting means is trained, the movably mounted prosthesis part and the pulley being detachably mounted on the drive connection, guide rollers for guiding the flexible elongated motion-transmitting means to the pulley.

13. A prosthesis comprising a stationary part and a part movably mounted on the stationary part, a drive unit mounted on the stationary part and a transmission for converting a rotary motion produced by the drive unit into a reciprocating linear motion for driving the movably mounted part, the transmission including a transmission member coupled to the drive unit for rotation therewith, the transmission member having two separate threads of opposite pitch, two transmission elements respectively threadedly mounted on a respective one of the threads of opposite pitch for linear movement in relation thereto, the transmission elements being non-rotatable in relation to the transmission member whereby rotation of the member causes the linear movement of the elements, a tackle with flexible elongated motion-transmitting means having two ends facing the drive unit, a respective one of the motion-transmitting means ends being affixed to a respective one of the transmission elements and the tackle being connected to the movably mounted prosthesis part for moving the same in response to the rotary motion of the drive unit, drive connection for the movably mounted prosthesis part, a bevel gearing comprising a driving and a driven bevel gear, and a pulley over which the flexible motion-transmitting means is trained, the driving bevel gear being mounted on the pulley for rotation therewith, and the driven bevel gear and the movably mounted prosthesis part being mounted on the drive connection.

14. A prosthesis comprising a stationary part and a part movably mounted on the stationary part, a drive unit mounted on the stationary part and a transmission for converting a rotary motion produced by the drive unit into a reciprocating linear motion for driving the movably mounted part, the transmission including a transmission member coupled to the drive unit for rotation therewith, the transmission member having two separate threads of opposite pitch, two transmission elements respectively threadedly mounted on a respective one of the threads of opposite pitch for linear movement in relation thereto, the transmission elements being non-rotatable in relation to the transmission member whereby rotation of the member causes the linear movement of the elements, a tackle with flexible elongated motion-transmitting means having two ends facing the drive unit, a respective one of the motion-transmitting means ends being affixed to a respective one of the transmission elements and the tackle being connected to the movably mounted prosthesis part for moving the same in response to the rotary motion of the drive unit, an end portion of the flexible elongated motion-transmitting means opposite the ends facing the drive unit being attached to different sides of the movably mounted prosthesis part for direct movement thereof in response to the movement of the transmitting means.

* * * * *